United States Patent [19]

Panzik et al.

[11] 4,266,540
[45] May 12, 1981

[54] NASAL OXYGEN THERAPY MASK

[76] Inventors: Donald Panzik, 47 Ballantine Rd., Rochester, N.Y. 14623; David Smith, P.O. Box 197, Avoca, N.Y. 14809

[21] Appl. No.: 951,744

[22] Filed: Oct. 13, 1978

[51] Int. Cl.³ .............................................. A61M 15/00
[52] U.S. Cl. ........................... 128/207.13; 128/207.12; 128/205.25; 128/205.11; 128/204.25
[58] Field of Search ............... 128/140 N, 140 R, 146, 128/146.5, 146.6, 195, 196, 197, 198, 205, 209, 210, 188, 203.23, 204.12, 204.25, 205.25, 207.13, 205.11, 207.12

[56] References Cited
U.S. PATENT DOCUMENTS

| | | | |
|---|---|---|---|
| 1,176,886 | 3/1916 | Ermold | 128/209 |
| 2,241,535 | 5/1941 | Boothby et al. | 128/206 |
| 2,260,701 | 10/1941 | Boothby et al. | 128/205 X |
| 2,843,122 | 7/1958 | Hudson | 128/207.13 |
| 2,859,748 | 11/1958 | Hudson | 128/207.13 |
| 3,603,306 | 9/1971 | Bonin | 128/145 A |
| 3,889,671 | 6/1975 | Baker | 128/206 |
| 3,977,432 | 8/1976 | Vidal | 128/210 |

Primary Examiner—Henry J. Recla
Attorney, Agent, or Firm—George E. Clark

[57] ABSTRACT

An oxygen mask which covers only a patient's nose is attached to the patient by a flexible strap. A clip is attached to the outer surface of the mask to hold the portion of the mask firmly in place relative to the bridge of the patient's nose. An exhaust port is included in the mask. The mask also includes an integral mixing valve for mixing air and gas such as oxygen to achieve a prescribed percentage mixture as may be required for patient therapy. The mixing valve is supported by a support member attached to the mounting strap.

4 Claims, 3 Drawing Figures

NASAL OXYGEN THERAPY MASK

BACKGROUND OF THE INVENTION

The present invention relates to an improved device for administering oxygen therapy and more particularly to an improved nasal mask for use in administering oxygen therapy.

In the prior art, there are many devices used for administering oxygen to a patient. Many of these oxygen masks cover both the nose and mouth of the patient, preventing the patient from performing oral functions while under oxygen therapy.

Also, there are in the prior art many nasal adapters for administering gas to a patient for a variety of purposes. Nasal adapters appear to be primarily directed towards administering anaesthesia.

Those nasal mask designed to administer anaesthesia do not include means for mixing air with a gas to achieve a predetermined percentage of the gas in the air delivered to the patient for breathing.

There are of course oxygen masks designed for masal application but these masks are for the most part, bulky, complex, and heavy and are not adaptable to an ambulatory patient who may require administration of oxygen therapy on a continuous basis such as a patient suffering from emphysema.

Examples of patents showing a prior art nasal anaesthesia administering mask are U.S. Pat. No. 1,189,716 to McKeeson; U.S. Pat. No. 3,889,671 to Baker; U.S. Pat. No. 1,206,045 to Smith; and U.S. Pat. No. 1,486,290 to Littauer.

A prior art patent which shows a nasal mask for delivering oxygen is U.S. Pat. No. 2,241,535 to Boothby, et. al.

All of the prior art which is know to applicants either is designed to by used for a different purpose, that is application of anaesthesia, or is bulky and complex and more expensive than a nasal mask according to applicants' invention.

SUMMARY OF THE INVENTION

It is, therefore, an objective of the present invention to deliver a mixture of gasses to a patient through a nasal mask which includes a mixing valve for mixing a pre-determined quantity of air with a gas to be administered for therapeutic benefit of the patient.

It is another object of the present invention to administer a mixture of gases to a patient as above with a nasal mask which includes an exhaust port for exhaled gases.

It is yet another object of the present invention to administer oxygen to a patient as above with a nasal oxygen mask including a mixing valve which mixes a pre-determined quantity of air with the oxygen supply to provide a prescribed percentage of oxygen in the air to be breathed by the patient.

In accordance with the present invention, a nasal mask is shaped to cover a patient's nose but not cover a patient's mouth. The mask is attached to the patient's head with a strap which may be of some flexible material. A nose grip is mounted at the outer bridge of the mask to firmly position the upper end of the mask relative to the patient's nose bridge. A mixing valve is integrally mounted with the mask to permit a prescribed amount of therapeutic gas to be mixed with air to be administered to the patient.

A nasal oxygen mask according to the present invention has the advantage of being inexpensive, light on the patient's face, and not abrasive of chafing to the patient.

These and other objects, features, and advantages of the present invention together with the operation of the invention will be fully understood by reference to the following detailed description, taken together with the accompanying drawings.

DETAILED DESCRIPTION OF THE INVENTION

Figure 1:
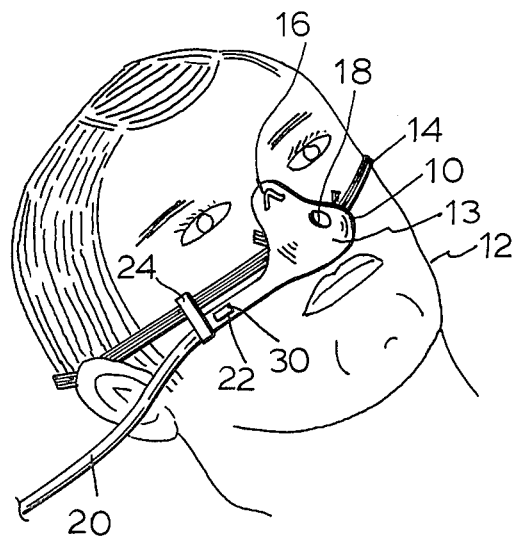
FIG. 1 is a perspective view showing a nasal oxygen mask according to the present invention attached to a patient.

Referring now to FIG. 1, a nasal oxygen mask according to a preferred embodiment of the present invention will be described. Mask 10 is attached to patient 12 by flexible strap 14. Mask 10 covers patient's nose 13. A flexible deformable clip 16 is mounted on outer bridge of mask 10 at such a position so that the clip may be used to position the mask relative to the bridge of the patient's nose 13. The clip may be made of aluminum or other deformable material. The mask 10 may be constructed of a variety of flexible plastic composition.

Mask 10 has a port 18 used for exhaling.

A therapeutic gas such as oxygen gas is supplied to mask 10 by supply tube 20 which is attached to mask 10 through mixing valve 22. At the point of connection between supply tube 20 and mixing valve 22, there is a support 24 which attaches the mixing valve supply tube connection to strap 14.

Figure 2:
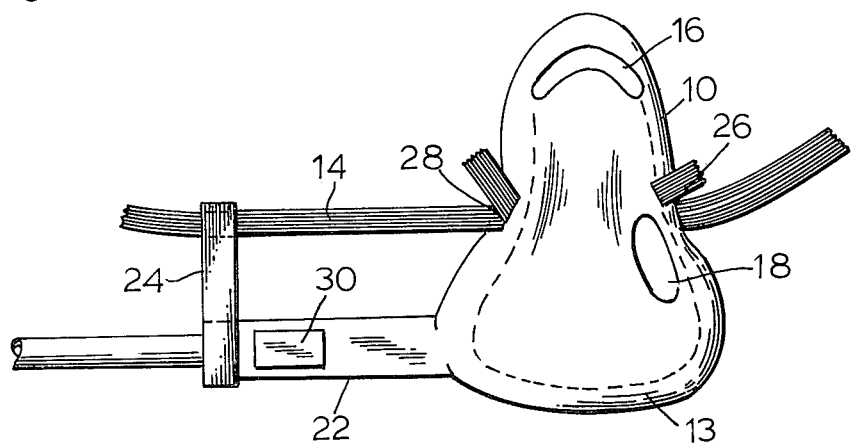
FIG. 2 is a view of an oxygen mask according to the present invention.

Referring now to FIG. 2, it is seen that strap 14 passes through slots 26 and 28 to support mask 10.

Support 24 may be of some light plastic material.

Figure 3:
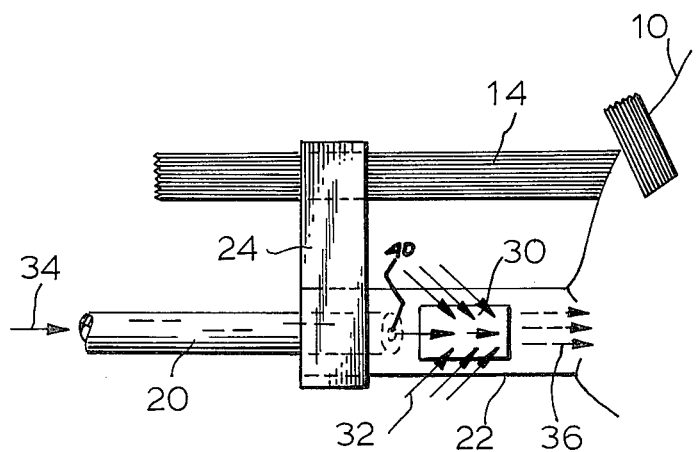
FIG. 3 is a detailed view of a mixing valve for mixing therapeutic gas with air in combination with a nasal oxygen mask according to the present invention.

Referring now to FIG. 3, mixing valve 22 will be described in greater detail. Mixing valve 22 has a hole 30 therein to allow room air to be drawn in and entrained with the flow of therapeutic gas such as oxygen. The ambient or room air 32, drawn in through opening 30, mixes with therapeutic gas 34 being applied through tubing 20 under pressure, such as 2 liters per minute of oxygen and results in a mixed gas 36 to be administered to a patient. The size of hole 40 determines the percentage of therapeutic gas such as oxygen in the mixture administered to the patient.

It should be noted that a variety of masks can be constructed each having a different size hole 40 for providing a pre-determined percentage mixture as required by prescription for individual patients. In a common oxygen therapy situation, it may be reasonable to provide as many as 10 different mask assemblies, each assembly having a different size opening 40 for providing a different gas mixture for patient therapy.

It should be further noted, that since the oxygen mask according to the present invention does not cover the patient's mouth oral functions may be performed by the patient without removing the mask. In some situations such as a patient suffering from emphysema, it is very important that the oxygen mask be in place nearly 100 percent of the time.

Further, an oxygen mask according to the present invention will reduce irritation and pressure sores which normally occurs with nasal cannulae.

While the present invention has been described with reference to a preferred embodiment thereof, it will be understood by those skilled in the art that various changes may be made in the embodiment of the invention without departing from the spirit or scope of the invention.

What is claimed is:

1. Apparatus for administering a select mixture of gases to a patient for therapeutic treatment, comprising:
    a mask shell generally adapted to fit over and cover a patient's nose while leaving the mouth free to perform oral functions, said mask shell having an opening therein for exhalation of gases by said patient; and
    a mixing valve connected to said mask shell, said mixing valve with said masked shell being formed as a one-piece structure, said mixing valve further comprising means for providing a stream of a therapeutic gas therethrough and into said mask shell, and a fixed aperature of predetermined size in a side of said mixing valve in communication with said stream to permit a predetermined volume of ambient air to be entrained into said mixing valve for mixing with said therapeutic gas, wherein dimensions of said aperature are selected to provide a fixed percentage of ambient air in a mixture of ambient air and said therapeutic gas whereby said apparatus can be prescribed by a physician to provide a precise therapeutic gas/air mixture to a patient.

2. Apparatus according to claim 1 further comprising means mounted on said mask shell for affixing said mask shell to an upper portion of said patient's nose.

3. Apparatus according to claim 1 further comprising a flexible strap attached to said mask shell on either side thereof and passing around said patient's head to hole said mask in place.

4. Apparatus according to claim 1 further comprising a support means attached to said flexible strap and to said mixing valve for supporting said mixing valve and said means for supplying a therapeutic gas to reduce torque placed on said mask shell by weight of said mixing valve and means for supplying a therapeutic gas.

* * * * *